United States Patent [19]

Leka

[11] Patent Number: 4,620,794
[45] Date of Patent: Nov. 4, 1986

[54] GRADIENT FORMERS

[75] Inventor: George T. Leka, Trumbull, Conn.

[73] Assignee: Jule Inc., Trumbull, Conn.

[21] Appl. No.: 673,278

[22] Filed: Nov. 20, 1984

[51] Int. Cl.$^4$ .......................... B01F 7/16; B01F 13/08; B01F 15/02

[52] U.S. Cl. .................................... 366/131; 222/137; 222/387; 366/160; 366/182; 366/194; 366/273

[58] Field of Search ............... 366/131, 134, 139, 143, 366/150, 160, 161, 162, 177, 182, 184, 194, 269, 273, 290; 222/137, 387

[56] References Cited

U.S. PATENT DOCUMENTS

| | | | |
|---|---|---|---|
| 2,131,488 | 9/1938 | Tear | 222/387 X |
| 3,443,520 | 5/1969 | Nejame, Jr. | 366/161 X |

FOREIGN PATENT DOCUMENTS

| | | | |
|---|---|---|---|
| 1161140 | 1/1964 | Fed. Rep. of Germany | 366/134 |
| 793277 | 4/1958 | United Kingdom | 222/137 |

*Primary Examiner*—Philip R. Coe
*Attorney, Agent, or Firm*—Mattern, Ware, Stoltz & Fressola

[57] ABSTRACT

By providing two, interconnected fluid storing containers, each of which comprise piston members sealingly engaged therewith and manually movable along the inside surface thereof, a unique, linear gradient former is achieved which is capable of controllably providing precisely mixed linear gradients. In addition, the linear gradient former of the present invention is usable to quickly, easily, and precisely fill the fluid holding chambers, by manually moving the pistons in an opposite direction. One of the fluid storing containers incorporates outlet means for delivering the linear gradient to the desired chamber for use and, in the preferred embodiment, also incorporates fluid mixing means to assure uniform distribution of the fluids in the container prior to being dispensed.

8 Claims, 8 Drawing Figures

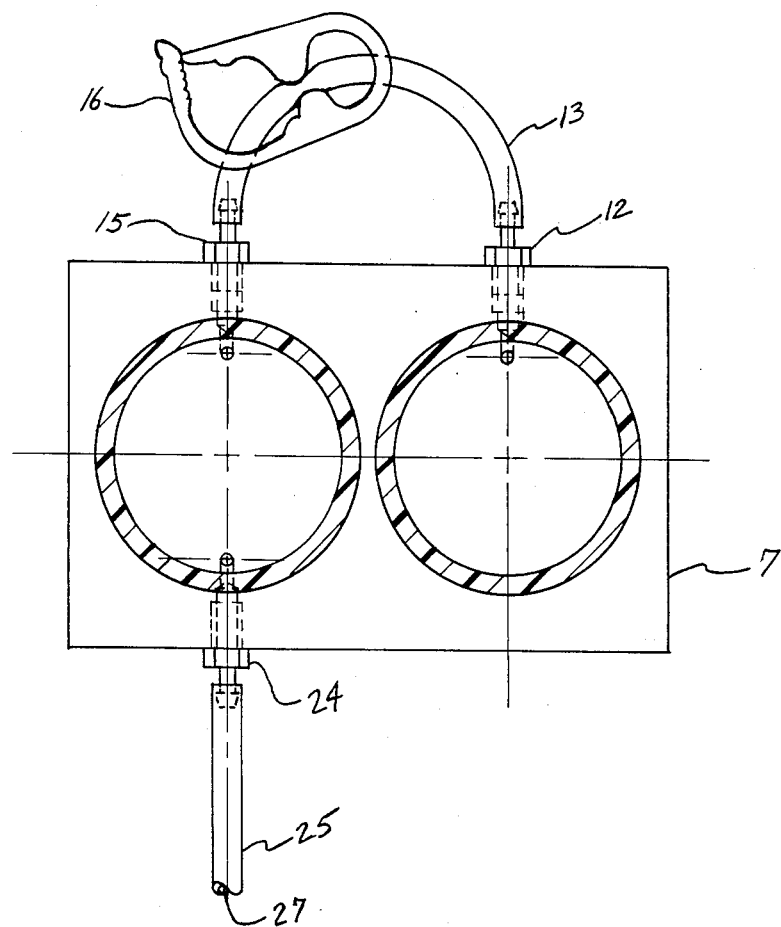
FIGURE 2
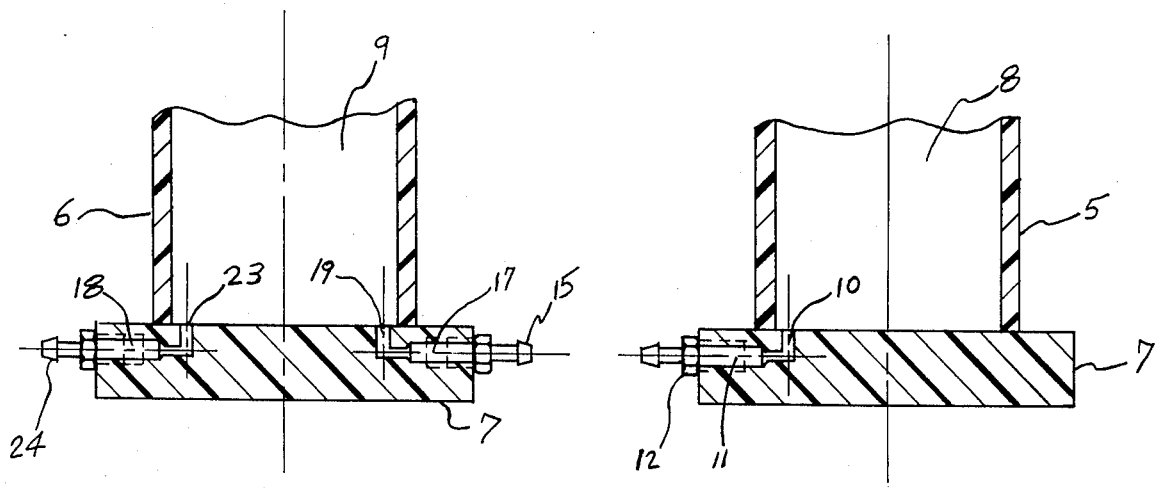
FIGURE 3
FIGURE 4

GRADIENT FORMERS

TECHNICAL FIELD

This invention relates to gradient formers, and more particularly to linear gradient formers.

BACKGROUND OF THE INVENTION

In general, gradient formers are used to mix two fluids together in either a linear or an exponential fashion. To make perfect linear gradients, the geometry of the two chambers must be identical and the fluid level must drop at the same rate in each chamber. During operation, the fluid flows from the reservoir chamber into the mixing chamber. The concentration of the stream of gradient exiting from the mixing chamber changes at a constant rate with respect to volume. The result is a perfectly linear gradient varying between two original limits. The gradient slope can be either positive or negative, depending upon the relative concentrations initially placed in the two chambers. Linear gradient formers are used in centrifugation, electrophoresis and liquid chromatography.

Prior art linear gradient formers of the dual chamber type are not capable of controlling the rate at which the fluid drops in each chamber; therefore, the gradients that are formed are *not* accurate. A prior art linear gradient former may work for fluids of one specific set of physical properties for which it was designed. However, prior art gradient formers are unable to compensate for fluids of different viscosity because their cylinders are open to the atmosphere. One typical use of linear gradient formers are used in centrifugation to create sucrose gradients in centrifuge rotor tubes or for continuous flow zonal rotors. Biological samples are separated via density gradient centrifugation. Accuracy of the density gradient is extremely important to obtaining a desired separation.

Gradient formers are also used to create the cast gels in electrophoresis applications.

In gravity flow column liquid chromatography, the gradient former is used for separation of pressure sensitive biological samples. The gradient former can also be used as a pre-pump gradient former for high performance, high pressure liquid chromatography.

Prior art linear gradient formers, which are used to fill centrifuge tubes, are inaccurate because their cylinders are open to the atmosphere and they cannot compensate for different fluids of different viscosities; therefore, the mixing is very inaccurate. These gradient formers are often used to fill centrifuge tubes. Typically, prior art gradient formers fill one tube at a time. Using a small syringe, the operator must manually refill the gradient former for each centrifuge tube. This is a slow, tedious, labor-intensive process, and the resulting gradients formed are inaccurate. Therefore, it is a principal object of the present invention to provide a gradient former which is capable of controlling the fluid level in each chamber regardless of the density or viscosity of the particular fluid.

Another object of the present invention is to provide a gradient former having the characteristic features described above which is capable of providing accurate linear gradients for all fluids regardless of the physical properties of the particular fluids being employed.

Another object of the present invention is to provide a linear gradient having the characteristic features described above which is capable of providing the operator with complete control over the fluid flow rate, and the resulting fluid level drop in each chamber.

A further object of the present invention is to provide a gradient former having the characteristic features described above which also provides for a quick and easy filling of the fluid chambers regardless of the volume to be filled.

Another object of the present invention is to provide a gradient former having the characteristic features described above which is capable of providing accurate linear gradients quickly and easily with equal efficacy regardless of the volumes required by the user.

Other and more specific objects will in part be obvious and will in part appear hereinafter.

SUMMARY OF THE INVENTION

The present invention is directed to a linear gradient former assembly, which is used to mix two liquids together in a linear fashion. The gradient former of this invention consists of two chambers for storing the two fluids prior to mixing. The two fluids to be mixed are initially placed in each one of the chambers. One chamber is called the storage chamber, and the other is the mixing chamber. A piston is inserted into each chamber. The two pistons are equal in length and they are attached to each other by a brace or handle.

The present invention has some of the following key features, which prior art inventions do not have;

A dual piston assembly used for a small size gradient former (under 500 ml), which can be manually operated to displace fluid at an equal rate in each chamber independent of fluid viscosity or density. Manual operation is possible because the force needed to depress the piston is low enough in small gradient formers to make manual operation practical and possible.

A manually operated piston assembly, which is more economical than a motorized version.

A small volume gradient former which can pump fluid downstream instead of relying upon gravity for flow.

A dual piston assembly which can be used to keep fluid level in each chamber equal to each other during a gravity flow gradient.

When the present invention is converted into an exponential gradient former with an adjustable mixing chamber volume, the storage chamber piston can be used to pump the gradient fluid downstream. The storage chamber piston can be retracted to refill the storage chamber as often as necessary to pump gradient downstream for large volume exponential gradients.

A dual piston assembly which is manually retractable for refilling both the mixing and storage chambers from an external reservoir. Fluids can be pre-mixed in external reservoirs and many gradients can be made by pumping and refilling from these reservoirs in a shorter amount of time than previously possible.

Dual pistons and cylinders are assembled as close as possible to minimize minor error effects due to rocking of the dual pistons during pumping.

The storage chamber consists of a cylinder attached to a base. Fluid exits the storage chamber through a hole in the base. Fluid from the storage chamber flows into the mixing chamber via flexible tubing. A hydraulic fitting is attached both to the storage chamber and the mixing chamber, which also contains a fitting and hole for fluid to enter the mixing chamber from the storage chamber. A tube clamp is used to shut off or restrict the flow from the storage chamber to the mixing chamber.

The mixing chamber cylinder is mounted to a base which consists of an entrance hole and an exit hole for fluid to enter and exit the mixing chamber. Hydraulic fittings are used for entrance and exit holes and flexible tubing is attached to the exit. A tube clamp is used to meter or shut off flow from the mixing chamber.

The mixing chamber and storage chamber each contain a piston with an o-ring seal. Each piston has a hole which extends from the piston face all the way through the piston handle. At the end of the hole in each of the piston handles there is a hydraulic fitting attached. Flexible tubing is connected to each hydraulic fitting in each of the two pistons. The flexible tubing coming from each piston is inserted into separate fluid reservoirs. When the pistons are retracted within their respective cylinders and the downstream or exit tubing is properly clamped, a vacuum is created in both chambers and fluid is sucked from the two reservoirs into the storage chambers. After the chambers are filled to the desired volume, the flexible tubing leading to the two reservoirs is clamped shut.

To begin mixing the two fluids in a linear fashion, the two downstream clamps are opened and the pistons are simultaneously used to force fluid out of the gradient former. Fluid from the storage chamber flows into the mixing chamber where it is mixed with the fluid in the mixing chamber. The resulting fluid from the mixing chamber exits as a linear mixture of the two fluids. A Teflon coated bar magnet is located in the mixing chamber. The bar magnet rotates and creates mixing when the gradient former is used with a typical magnetic stirrer, a common laboratory device.

After the two chambers have been emptied by using the dual pistons to push out the fluids, the chambers can be rinsed by sucking fluid into the chambers via the mixing chamber exit hole. Rinsing is accomplished by retracting and pumping the dual piston assembly until the cylinders are rinsed. Sucking air on the final strokes forces out any remaining liquid in the storage and mixing chambers. When the two chambers are cleared of liquid, the downstream clamps are closed and the upstream clamps are opened. Fluid can be sucked from each reservoir to fill the storage and mixing chambers respectively by retracting the pistons to the desired volume in the cylinder. Excess air between pistons and liquid surfaces is pumped backed into the reservoir and the upstream clamps are shut off. The linear gradient former is now ready to begin a new cycle of mixing the two fluids in a linear fashion.

The invention accordingly comprises the features of construction, combinations of elements and arrangement of parts which will be exemplified in the constructions hereinafter set forth, and the scope of the invention will be indicated in the claims.

THE DRAWINGS

For a fuller understanding of the nature and objects of the present invention, reference should be had to the following detailed description taken in connection with the accompanying drawings, in which:

FIG. 2 is a top plan view, partially in cross section, of the linear gradient former of the present invention taken along line 2—2 of FIG. 1;

FIG. 3 is a cross-sectional elevation view, partially broken away, of the gradient former of the present invention taken along line 3—3 of FIG. 1;

FIG. 4 is a cross-sectional elevation view, partially broken away, of the gradient former of the present invention taken along line 4—4 of FIG. 1;

DETAILED DESCRIPTION OF THE PREFERRED EMBODIMENTS

Figure 1:
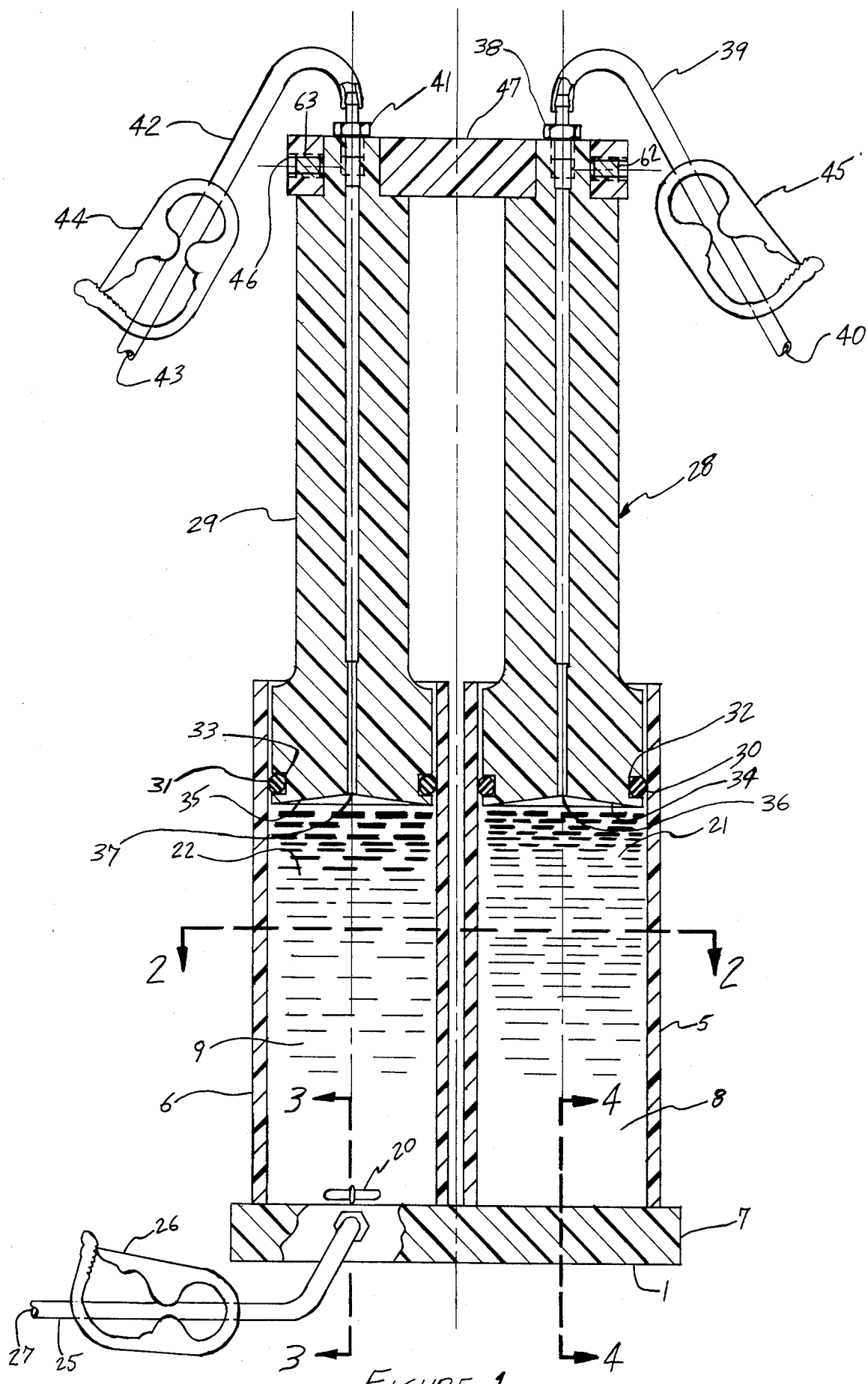
FIG. 1 is a cross-sectional elevation view detailing the linear gradient former of the present invention.

As shown in FIGS. 1 & 2, linear gradient former assembly 1 comprises two identical cylinders 5 & 6. Cylinder 5 is mounted to a base 7, and thereby forms a storage chamber 8. Cylinder 6 is also mounted to base 7, thereby forming a mixing chamber 9. Base 7 contains an exit portal 10, shown in FIG. 4, perpendicular to the base 7 and located within cylindrical wall 5. A radial hole 11 in base 7 connects to the perpendicular portal 10. A fitting 12 is assembled into hole 11, and flexible hose or tubing 13 is attached to fitting 12. In this way, any fluid contained in cylinder 5 is able to exit storage chamber 8 through the portal 10, connecting hole 11 and fitting 12 into hose 13.

Storage chamber tubing 13 is connected to mixing chamber 9 by a fitting 15. In addition, a tube clamp 16 is positioned along tubing 13 in order to controllably shut off or meter the flow rate between storage chamber 8 and mixing chamber 9. If desired, a metering valve could be used instead of a clamp 16 to restrict flow rate.

Using a configuration similar to the construction detailed above and best seen in FIGS. 3 & 4, mixing chamber base 7 also contains radial holes 17 and 18 formed therein substantially opposite each other. In addition, portals 19 and 23 are formed in base 7 within cylindrical wall 6. Portal 19 connects to radial hole 17 while portal 23 connects to radial hole 18. In this way, fluid from storage chamber 8 is able to enter mixing chamber 9 through hole 17 and portal 19, and exit chamber 9 through portal 23 and hole 18.

Once the fluid is inside the mixing chamber 9, continuous mixing thereof takes place by the rotation of a teflon coated magnetic bar stirrer 20. Preferably, gradient former assembly 1 is mounted on a magnetic mixer which causes bar stirrer 20 to rotate during gradient forming operation. After fluids 21 and 22 are mixed, the fluids exit mixing chamber 9 through portal 23, which meets with hole 18. A haudraulic fitting 24 is assembled to hole 18 and flexible tubing 25 is connected to fitting 24. A tube clamp 26 is used to shut off or restrict the flow from mixing chamber 9. After fluids 21 and 22 mix, they exit via hole 27 in flexible tubing 25. If desired, a metering valve could be sustituted for clamp 26 in order to shut off or create a restriction to flow rate.

The last major component of gradient former assembly 1 of the present invention is the piston assembly. The piston assembly consists of two identical pistons 28 and 29. Pistons 28 and 29 utilize o-ring seals 30 and 31, which are held in place by o-ring grooves 32 and 33. Piston 28 is inserted into cylinder 5 and piston 29 is inserted into cylinder 6. Pistons 28 and 29 preferably incorporate conical shaped end faces 34 and 35, which are shaped to encourage air bubbles and liquid to enter into portal 36 of piston 28 and portal 37 of piston 29. Portal 36 runs axially through the center of piston 28, where fitting 38 is attached to the top of piston 28. Flexible tube 39 is attached to fitting 38 and tube 39 is used to carry fluid through hole 40 of tube 39 from a reservoir, which holds the fluid for storage chamber housed by cylinder 5 of linear gradient former assembly 1.

Portal 37 runs axially through the center of piston 29, where fitting 41 is attached to top of piston 29. Flexible tube 42 is attached to fitting 41 and tube 42 is used to carry fluid through hole 43 of tube 42 from a second reservoir, which holds fluid for mixing chamber 9, housed by cylinder 6 of linear gradient former assembly 1. A tube clamp 44 is used to open or shut off flow in flexible tube 42. Tube clamp 45 is used to open or shut off flow in tube 39.

Gravity Flow

In some cases gravity flow from a gradient former is desirable, such as in low pressure column chromatography, where fluid pressures much greater than atmospheric pressure can destroy sensitive samples for biotechnology applications.

The present invention can be used to make an accurate gravity flow linear gradient because the fluid level in each chamber can be controlled to drop at the same rate by venting air into or out of each of the chambers.

For a gravity flow gradient, the linear gradient former is arranged as shown in FIG. 1. After chambers 8 and 9 are filled with liquids 21 and 22, flexible tubes 39 and 42 are removed from their respective reservoirs. Screw clamps or metering type valves should be substituted for tube clamps 44 and 45. The gravity flow linear gradient is started by opening the downstream clamps 26 and 16. The level of fluids 21 and 22 is controlled to drop at the same rate by venting air into or out of chambers 8 and 9 through holes 40 and 43, which connect to holes 36 and 37. Dual piston assembly 47 can be pushed into cylinders 5 and 6 to assure the fluid levels in each chamber drop at the same rate. As the dual piston assembly 47 is pushed downward, air is vented out of chambers 8 and 9, and little or no pressure is exerted on fluids 21 and 22. Since pistons 28 and 29 are equal in length, they provide a means to aid the eye in assuring the liquids 21 and 22 drop at the same rate in each chamber.

Preferably, the reservoirs and mixing chamber cylinders are made of clear material such as clear acrylic, glass, polycarbonate, or other machinable or moldable material. A chemical resistant material may be necessary in some cases. To aid the operator in viewing and comparing the fluid level in each chamber, level rod 58 can be used instead of piston assembly 47. Level rod 58 slides up and down wires 59 and 60, which are attached by their ends to cylinders 5 and 6.

Figure 5:
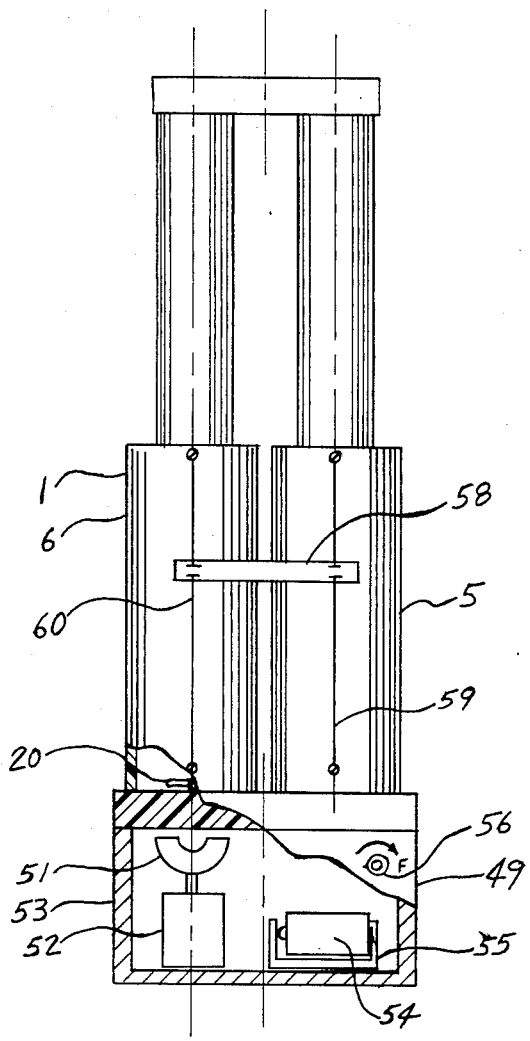
FIG. 5 is an elevation view, partially in cross-section, of an alternate embodiment of the linear gradient former of the present invention.
Figure 6:
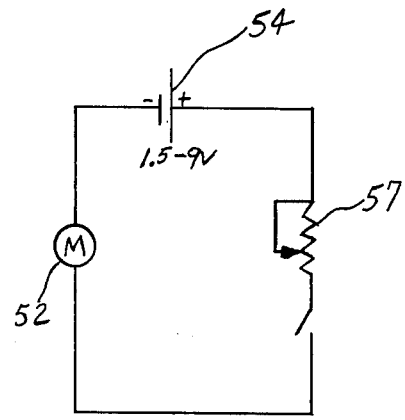
FIG. 6 is a schematic electrical drawing showing the operation of the electrical stirrer depicted in FIG. 5.

To make perfect linear gradients, the geometry of the two chambers must be identical and the fluid level must drop at the same rate in each chamber during operation. During operation, liquid flows from the storage chamber into the mixing chamber. The concentration of the stream of gradient exiting from the mixing chamber changes at a constant rate with respect to volume. The result is a perfectly linear gradient varying between the two original limits. The gradient slope can be either positive or negative, depending upon the relative concentrations initially placed in the two chambers. Linear gradients can be described by the following mathematical relationship (See reference 1):

$$Ct = Cm + (Cr - Cm)(Vt/2Vo)$$

where;
$Ct$ = Concentration of gradient being delivered at any time t
$Cm$ = Starting concentration in mixing chamber
$Cr$ = Starting concentration in reservoir
$Vt$ = Volume of gradient already withdrawn at time t
$Vo$ = Original volume in each chamber In FIG. 5 a gradient former 1 is shown mounted on top of magnetic mixer assembly 49. In its preferred embodiment, magnetic stirrer assembly is battery operated for portability, safety, low cost and design simplicity, although electricity from an alternating current source could also be substituted. Magnetic stirrer assembly 49 consists of magnet 51, which is mounted to shaft of motor 52, and motor 52 is attached to housing 53. Motor 52 is powered by battery 54, which is held by battery holder 55, which is attached to housing 53. Knob 56 controls speed of motor 52, which rotates magnet 51. Magnet 51 causes Teflon-coated bar magnet 20 to rotate via its rotating magnetic field. Knob 56 rotates a potentiometer 57, which controls speed of motor 52, as described by FIG. 6.

Exponential Gradient Forming

Figure 7:
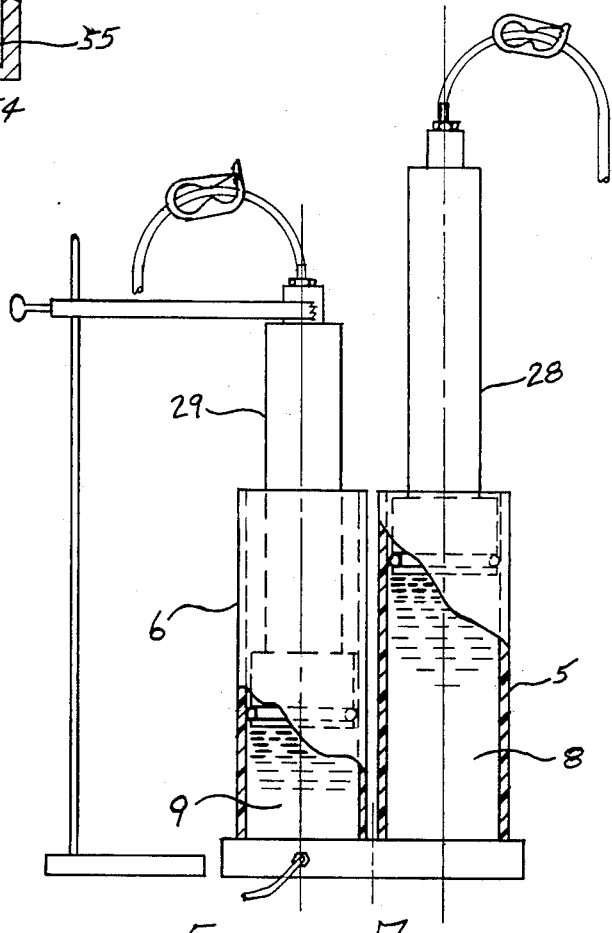
FIG. 7 is an elevation view, partially broken away, showing the gradient former of the present invention arranged for obtaining exponential gradients.

In FIG. 7, the preferred embodiment for an exponential gradient former is shown. In this embodiment, clamps 16 and 26 are closed off prior to filling chambers 8 and 9. Piston 29 is inserted into cylinder 6 and chamber 9 is filled with fluid 22 to desired volume via sucking fluid from reservoir via tubing 42. Piston 29 is held in place by a laboratory stand. Once volume of chamber 9 is established by piston 29 and cylinder 6, piston 29 does not move during exponential gradient forming. Piston 28 is inserted into cylinder 5, forming chamber 8. Chamber 8 is filled with fluid 21, as explained previously in FIGS. 1, 2, 3 and 4. To refill chamber 8 to continue exponential gradient, the two downstream clamps 16 and 26 are closed and clamp 45 is opened. Retracting piston 28 causes fluid to be sucked from the reservoir via hole 40 into chamber 8. Exponential gradient can be continued by opening or closing the correct valves, as previously explained. A new gradient can be made by repeating the above cycle.

An exponential gradient is produced by withdrawing liquid from the mixing chamber, the volume of which is kept constant. Liquid flows into the mixing chamber from the storage chamber, where the volume is allowed to diminish. If the mixing chamber contains the liquid of lesser concentration, the resulting gradient profile is convex exponential. If the mixing chamber contains the higher density liquid, the resulting profile is concave exponential. The smaller the volume of the mixing chamber, the more convex or concave the gradient. Exponential gradients can be described by the following relationship (See reference 1);

$$Ct = Cr - (Cr - Cm) e\uparrow -(Vt/Vm)$$

where;

e = natural base (i.e. 2.718)
Vm = volume of mixing chamber
↑ means that e is raised to the power of $-(Vt/Vm)$.

Reference 1, "Centrifugation in Biology and Medical Science", by Phillip Sheeler.

Gravity Flow Large Volume Linear Gradient Former

Figure 8:
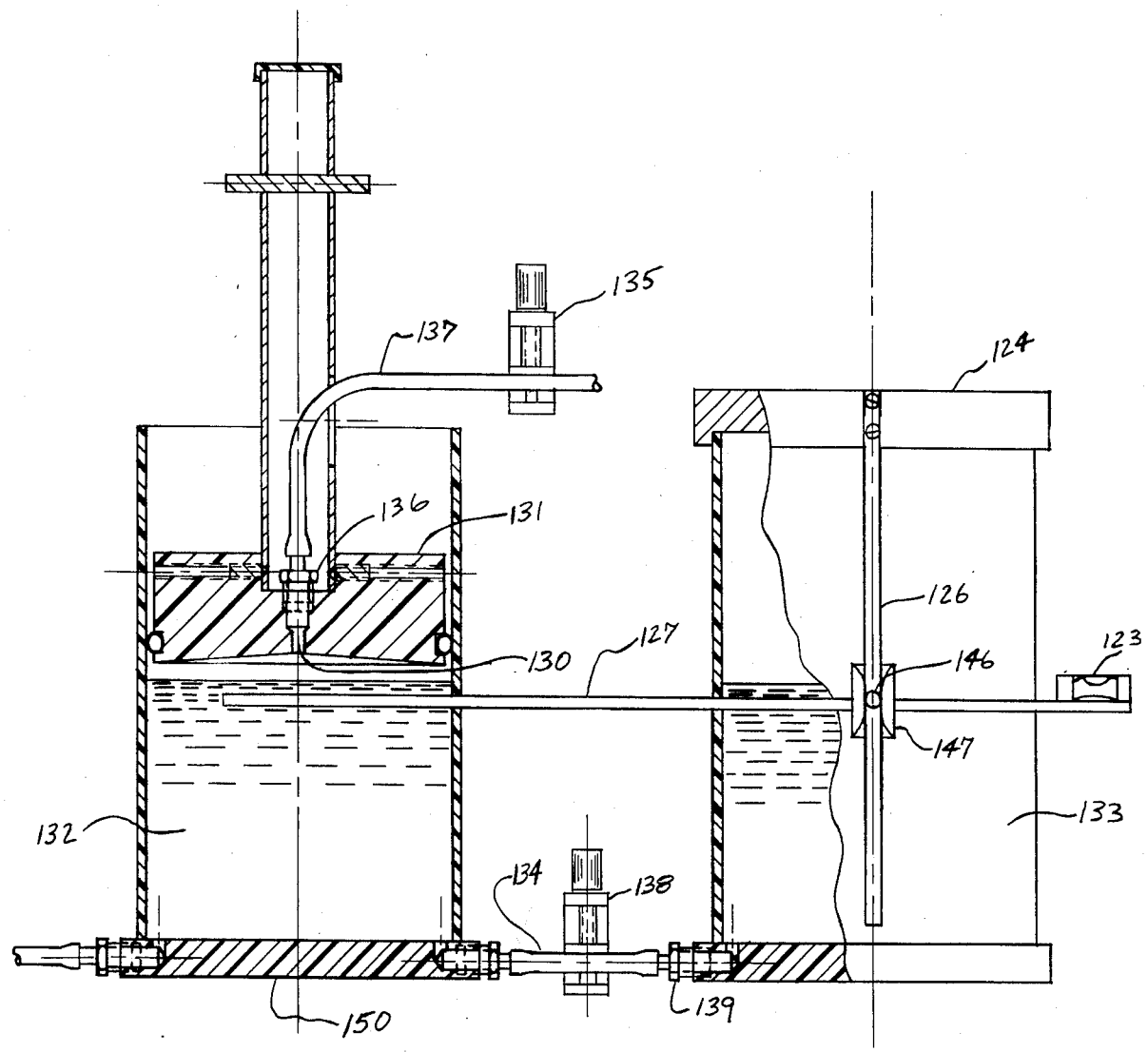
FIG. 8 is a cross-sectional elevation view, partially broken away, of an alternate embodiment of the linear gradient former for large volume gradients, where a sight leveling rod is employed.

In many cases a large volume linear gradient former is required, however, a manually operated dual piston assembly is not practical because the friction forces created by the two large piston o-ring seals would be too high for the ordinary lab technician to overcome routinely. Generally cylinder diameters of greater than 2.5 inches would be too high for frequent manual operation. One way to overcome this problem is to use gravity flow and only one piston in the mixing chamber as shown in FIG. 8. The fluid level in each chamber can be controlled by venting air into or out of the mixing chamber through hole 130 in piston 131. In its preferred embodiment the mixing chamber 132 and storage chamber 133 are on separate bases and connected by flexible tubing 134 as a linear gradient former as shown in FIG. 8.

In FIG. 8 the mixing chamber fluid level is controlled by the air vent hole 130 in the piston 131, where hydraulic fitting 136 and flexible tubing 137 are also connected and the tube screw clamp 135 is used to meter the rate air enters the mixing chamber. If air is vented rapidly, then the fluid level moves rapidly. Proper adjustment of air vent valve 135 enables the operator to control the rate fluid drops in the mixing chamber. The operator views and compares the fluid level in each chamber to assure fluids are dropping at the same rate. Adjustments are made to the vent valve, if necessary. In some cases, when forming density gradients, it may be necessary to throttle the flow rate using screw clamp 138 of the fluid coming from the storage chamber if the storage chamber fluid density is much greater than the density of the fluid in the mixing chamber.

A movable fluid level comparing rod spans across the front of the storage and mixing chambers to aid in assuring that the fluid in each chamber are identical.

In FIG. 8, to aid the operator in keeping the two fluid levels equal as the fluids drop by gravity flow, an elongated alignment rod 127 is provided. Rod 127 preferably pivots about the axis defined by holding pin 146. In addition, a bubble leveling device 123 is used to assure position rod 127 is perfectly horizontal. Preferably, level device 123 is positioned away from pivot pin 146 to create a counter balance of the weight of rod 127.

In addition to rod 127, the fluid level control assembly also incorporates a slider 147 and a rod supporting arm 126. Slider 147 incorporates pin 146 and securely retains rod 127. In addition, slider 146 is movably mounted to arm 126 for sliding movement along the entire length thereof. Preferably, arm 126 is attached to the storage chamber cover 124.

In addition, friction between slide 147 and arm 126 is sufficient to hold alignment rod 127 and level device 123 in place during normal use at any position along the length of arm 126.

Linear gradient former 150, FIG. 8, is mounted on separate bases so it can be converted into an exponential gradient former. An exponential gradient former is made by elevating the storage chamber 133 above the mixing chamber 132 and placing storage chamber 133 on a pedestal. Fitting 139 is connected to flexible tubing 137 and tube clamp 138 is closed. Fluid flows from chamber 133 into chamber 132 where it is mixed and it exits as an exponential gradient. The fluid leveling apparatus is not needed for exponential gradient forming.

It will thus be seen that the objects set forth above, among those made apparent from the preceding description, are efficiently attained and, since certain changes may be made in the above constructions, without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Having described my invention, what I claim as new and desire to secure by Letters Patent is:

1. A linear gradient former constructed for manually dispensing small volumed linear gradients and manually refilling the gradient former simultaneously from separate reservoirs comprising A. a first, elongated fluid storing container incorporating outlet means connected substantially at the base thereof;

B. a second elongated fluid mixing chamber incorporating inlet means and outlet means at the base thereof, with said inlet means interconnected with the outlet means of the first container;

C. a first pair of fluid flow control means mounted along the outlet means of the storage chamber and the outlet means of the mixing chamber;

D. a first piston member sealingly engaged with the first, elongated fluid storing container and incorporating
  a. a first, container engaging portion,
  b. a first, elongated rod portion extending from the first container-engaging portion and comprising a length at least equal to the length of said container, providing a readily accessible, easily controlled member for use by the operator to manually move the container engaging portion along the entire length of said container,
  c. channel means formed in said first elongated rod portion and said first container engaging portion, providing a first elongated, continuous fluid carrying conduit extending the entire length of said first piston member, and
  d. tube means extending from said first fluid carrying elongated conduit, providing a fluid flow path directly into or out of said first fluid storing container directly through said first piston member;

E. a second piston member sealingly engaged with the second, elongated, fluid mixing chamber and incorporating
  a. a second, container engaging portion
  b. a second, elongated rod portion extending from the second container-engaging portion and comprising a length at least equal to the length of said container, providing a readily accessible, easily controlled member for use by the operator to manually move the second container engaging portion along the entire length of said container,
  c. channel means formed in said second elongated rod portion and said second container engaging portion, providing a second elongated, continuous fluid carrying conduit extending the entire length of said second piston member, and d. tube means extending from said second fluid carrying conduit, providing a fluid flow path directly into or out of said second fluid mixing chamber directly through said second piston member;

F. a second pair of fluid flow control means mounted along the tube means of said first and second piston members for controlling the flow of fluid through said piston members, thereby providing means for venting or controlling air pockets above liquids in said chambers prior to gradient formations, as well as providing means for filling said chambrrs with desired liquids simultaneously from separate reservoirs;

G. handle means removably mounted to the elongated rod portions of said first and second piston members and extending therebetween, providing a readily accessible handle for use by the operator in simultaneously manually moving both piston members the entire length of said containers with precision and accuracy; whereby the rate of fluid flow from the first, fluid storing container into the second fluid-mixing container and the rate of fluid flow out of the fluid-mixing container are precisely controlled, directly by the operator, throughout the entire dispensing of the gradient, assuring that fluid levels drop at the same rate in each chamber, while also providing controlled, manual refilling of both chambers simultaneously, from separate reservoirs, by manually moving said piston members in the opposite direction and allowing fluid to flow simultaneously into the chambers from separate reservoirs through said tube means and fluid conduits formed in said piston members.

2. The linear gradient former defined in claim 1, wherein each of the first and second containers are further defined as comprising substantially identical regular cylindrical shapes and the first and second piston members are further defined as comprising e. a first, container-engaging portion having a substantially cylindrical shape with a diameter substantially equal to the inner diameter of the cylindrically-shaped container, and f. an O-ring retaining groove and sealing ring mounted therein for assuring sealing engagement of the container-engaging portion of the piston member and walls of the container.

3. The linear gradient former defined in claim 2, wherein said container engaging portions of said piston members each comprise a tapered end face positioned in juxtaposed, spaced facing relationship with the fluid in the container, said face being tapered away from the fluid level, thereby providing an air pocket above the fluid level.

4. The linear gradient former defined in claim 2, wherein said first and second containers are further defined as being mounted to a common support base, in juxtaposed, closely spaced cooperating relationship with each other, thereby providing ease of visual comparison of the fluid levels in each container.

5. The linear gradient former defined in claim 1, wherein said second, fluid mixing container is further defined as incorporating stir means for assuring proper mixing of the fluid contained therein.

6. The linear gradient former defined in claim 5 wherein said stir means is further defined as comprising a rotatable bar magnet mounted below said base in controlled relationship with a stirring rod mounted in the cylinder thereby providing continuous stirring of the fluids in the mixing cylinder.

7. The gradient former defined in claim 1, further comprising

H. an adjustable sighting rod
   a. extending between said first and second elongated containers, substantially perpendicularly to the central axes thereof; and
   b. laterally movable along the length of said containers, thereby providing easily adjustable liquid level comparing means to assure the liquid level in both containers are maintained at substantially identical levels.

8. A linear gradient former constructed for manually dispensing small volumed linear gradients and manually refilling the gradient former simultaneously from separate reservoirs comprising A. a first, elongated, substantially cylindrically-shaped, fluid storing container incorporating outlet means connected substantially at the base thereof;

B. a second, elongated, substantially cylindrically-shaped, fluid mixing chamber incorporating inlet means and outlet means at the base thereof, with said inlet means interconnected with the outlet means of the first container;

C. a container supporting base,
   a. securely supportingly retaining said first and second containers fixedly thereon, and
   b. having conduit means formed therein, defining said inlet and outlet means of said containers;

D. a first pair of fluid flow control means mounted along the outlet means of the storage chamber and the outlet means of the mixing chamber;

E. a first piston member sealingly engaged with the first, elongated fluid storing container and incorporating
   a. a first, container engaging portion having a substantially cylindrical shape with a diameter substantially equal to the inner diameter of the cylindrically-shaped container,
   b. an O-ring retaining groove and sealing ring mounted therein for assuring sealing engagement of the container-engaging portion of the piston member with the walls of the container,
   c. a first, elongated rod portion extending from the first container-engaging portion and comprising a length at least equal to the length of said container, providing a readily accessible, easily controlled member for use by the operator to manually move the container engaging portion along the entire length of said container,
   d. channel means formed in said first elongated rod portion and said first container engaging portion, providing a first elongated, continuous fluid carrying conduit extending the entire length of said first piston member, and
   e. tube means extending from said first fluid carrying elongated conduit, providing a fluid flow path directly into or out of said first fluid storing container through said first piston member;

F. a second piston member sealingly engaged with the second, elongated, fluid mixing chamber and incorporating
   a. a second, container engaging portion having a substantially cylindrical shape with a diameter substantially equal to the inner diameter of the cylindrically-shaped container,
b. an O-ring retaining groove and sealing ring mounted therein for assuring sealing engagement of the container-engaging portion of the piston member with the walls of the container,
d. a second, elongated rod portion extending from the second container-engaging portion and comprising a length at least equal to the length of said container, providing a readily accessible, easily controlled member for use by the operator to manually move the second container engaging portion along the entire length of said container,
d. channel means formed in said second elongated rod portion and said second container engaging portion, providing a second elongated, continuous fluid carrying conduit extending the entire length of said second piston member, and
e. tube means extending from said second fluid carrying conduit, providing a fluid flow path directly into or out of said second fluid mixing chamber through said second piston member;
G. a second pair of fluid flow control means mounted along the tube means of said first and second piston members for controlling the flow of fluid through said piston members, thereby providing means for venting or controlling air pockets above liquids in said chambers prior to gradient formations, as well as providing means for filling said chambers with desired liquids simultaneously from separate reservoirs; and
H. handle means removably mounted to the elongated rod portions of said first and second piston members and extending therebetween, providing a readily accessible handle for use by the operator in simultaneously manually moving both piston members the entire length of said containers with precision and accuracy;

whereby the rate of fluid flow from the first, fluid storing container into the second fluid-mixing container and the rate of fluid flow out of the fluid-mixing container are precisely controlled, directly by the operator, throughout the entire dispensing of the gradient, assuring that fluid levels drop at the same rate in each chamber, while also providing controlled, manual refilling of both chambers simultaneously, from separate reservoirs, by manually moving said piston members in the opposite direction and allowing fluid to flow simultaneously into the chambers from separate reservoirs through said tube means and fluidconduits formed in said piston members.

* * * * *